(12) United States Patent
Heruth et al.

(10) Patent No.: US 7,395,113 B2
(45) Date of Patent: Jul. 1, 2008

(54) COLLECTING ACTIVITY INFORMATION TO EVALUATE THERAPY

(75) Inventors: Kenneth T. Heruth, Edina, MN (US);
Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 276 days.

(21) Appl. No.: 10/825,965

(22) Filed: Apr. 15, 2004

(65) Prior Publication Data
US 2005/0209644 A1    Sep. 22, 2005

Related U.S. Application Data

(60) Provisional application No. 60/553,778, filed on Mar. 16, 2004.

(51) Int. Cl.
*A61N 1/00* (2006.01)
(52) U.S. Cl. .............................. 607/3; 607/48
(58) Field of Classification Search ............. 607/46, 607/48, 3, 9; 600/587, 585
See application file for complete search history.

(56) References Cited

U.S. PATENT DOCUMENTS

| | | | |
|---|---|---|---|
| 4,297,685 A | 10/1981 | Brainard, II | |
| 4,543,955 A | 10/1985 | Schroeppel | |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |
| 5,125,412 A | 6/1992 | Thornton | |
| 5,154,180 A | 10/1992 | Blanchet et al. | |
| 5,233,984 A * | 8/1993 | Thompson | 607/18 |
| 5,275,159 A | 1/1994 | Griebel | |

(Continued)

FOREIGN PATENT DOCUMENTS

DE      198 31 109      1/2000

(Continued)

OTHER PUBLICATIONS

"Watch," Wikipedia, the free encyclopedia, 6 pgs., http://en.wikipedia.org/wiki/Watch, (2006).

(Continued)

*Primary Examiner*—Carl Layno
*Assistant Examiner*—Brian T. Gedeon
(74) *Attorney, Agent, or Firm*—Shumaker & Sieffert, P.A.

(57) ABSTRACT

A medical device delivers a therapy to a patient. The medical device may periodically determine an activity level of the patient, and associate each determined activity level with a current therapy parameter set. A value of at least one activity metric is determined for each of a plurality of therapy parameter sets based on the activity levels associated with that therapy parameter set. A list of the therapy parameter sets is presented to a user, such as a clinician, for evaluation of the relative efficacy of the therapy parameter sets. The list may be ordered according to the one or more activity metric values to aid in evaluation of the therapy parameter sets. Where values are determined for a plurality of activity metrics, the list may be ordered according to the one of the activity metrics selected by the user.

61 Claims, 7 Drawing Sheets

U.S. PATENT DOCUMENTS

| | | | |
|---|---|---|---|
| 5,335,657 A | 8/1994 | Terry, Jr. et al. | |
| 5,337,758 A | 8/1994 | Moore et al. | |
| 5,342,409 A | 8/1994 | Mullett | |
| 5,469,861 A | 11/1995 | Piscopo et al. | |
| 5,476,483 A | 12/1995 | Bornzin et al. | |
| 5,514,162 A * | 5/1996 | Bornzin et al. | 607/19 |
| 5,593,431 A | 1/1997 | Sheldon | |
| 5,622,428 A | 4/1997 | Bonnet | |
| 5,645,053 A | 7/1997 | Remmers et al. | |
| 5,732,696 A | 3/1998 | Rapoport et al. | |
| 5,782,884 A | 7/1998 | Stotts et al. | |
| 5,832,932 A | 11/1998 | Elsberry et al. | |
| 5,895,371 A | 4/1999 | Levitas et al. | |
| 5,904,708 A | 5/1999 | Goedeke | |
| 5,904,780 A | 5/1999 | Tomoyasu | |
| 5,919,149 A | 7/1999 | Allum | |
| 5,941,906 A | 8/1999 | Barreras, Sr. et al. | |
| 5,944,680 A | 8/1999 | Christopherson et al. | |
| 6,044,297 A | 3/2000 | Sheldon et al. | |
| 6,045,513 A | 4/2000 | Stone et al. | |
| 6,059,576 A | 5/2000 | Brann | |
| 6,095,991 A | 8/2000 | Krausman et al. | |
| 6,102,874 A * | 8/2000 | Stone et al. | 600/595 |
| 6,120,467 A | 9/2000 | Schallhorn | |
| 6,128,534 A | 10/2000 | Park et al. | |
| 6,157,857 A | 12/2000 | Dimpfel | |
| 6,165,143 A | 12/2000 | van Lummel | |
| 6,259,948 B1 | 7/2001 | Florio et al. | |
| 6,280,409 B1 | 8/2001 | Stone et al. | |
| 6,296,606 B1 | 10/2001 | Goldberg et al. | |
| 6,308,098 B1 | 10/2001 | Meyer | |
| 6,351,672 B1 | 2/2002 | Park et al. | |
| 6,366,813 B1 | 4/2002 | DiLorenzo | |
| 6,416,471 B1 | 7/2002 | Kumar et al. | |
| 6,440,090 B1 | 8/2002 | Schallhorn | |
| 6,449,508 B1 * | 9/2002 | Sheldon et al. | 607/19 |
| 6,459,934 B1 | 10/2002 | Kadhiresan | |
| 6,466,821 B1 | 10/2002 | Pianca et al. | |
| 6,468,234 B1 | 10/2002 | Van der Loos et al. | |
| 6,514,218 B2 | 2/2003 | Yamamoto | |
| 6,539,249 B1 | 3/2003 | Kadhiresan et al. | |
| 6,574,507 B1 | 6/2003 | Bonnet | |
| 6,605,038 B1 | 8/2003 | Teller et al. | |
| 6,611,783 B2 | 8/2003 | Kelly, Jr. et al. | |
| 6,659,968 B1 * | 12/2003 | McClure | 600/595 |
| 6,687,538 B1 | 2/2004 | Hrdlicka et al. | |
| 6,731,984 B2 | 5/2004 | Chu et al. | |
| 6,752,766 B2 | 6/2004 | Kowallik et al. | |
| 6,773,404 B2 | 8/2004 | Poezevera et al. | |
| 6,819,956 B2 * | 11/2004 | DiLorenzo | 607/45 |
| 6,878,121 B2 | 4/2005 | Krausman et al. | |
| 6,881,192 B1 | 4/2005 | Park | |
| 6,884,596 B2 | 4/2005 | Civelli et al. | |
| 6,890,306 B2 | 5/2005 | Poezevera | |
| 6,928,324 B2 | 8/2005 | Park et al. | |
| 6,964,641 B2 | 11/2005 | Cho et al. | |
| 7,151,961 B1 | 12/2006 | Whitehurst et al. | |
| 7,155,279 B2 | 12/2006 | Whitehurst et al. | |
| 7,162,304 B1 | 1/2007 | Bradley | |
| 7,167,751 B1 | 1/2007 | Whitehurst et al. | |
| 7,209,787 B2 | 4/2007 | DiLorenzo | |
| 2001/0037067 A1 | 11/2001 | Tchou et al. | |
| 2002/0077562 A1 | 6/2002 | Kalgren et al. | |
| 2002/0091308 A1 | 7/2002 | Kipshidze et al. | |
| 2002/0161412 A1 | 10/2002 | Sun et al. | |
| 2002/0169485 A1 | 11/2002 | Pless et al. | |
| 2002/0177882 A1 | 11/2002 | DiLorenzo | |
| 2002/0193697 A1 | 12/2002 | Cho et al. | |
| 2002/0193839 A1 | 12/2002 | Cho et al. | |
| 2003/0004423 A1 | 1/2003 | Lavie et al. | |
| 2003/0139692 A1 | 7/2003 | Barrey et al. | |
| 2003/0149457 A1 | 8/2003 | Tcheng et al. | |
| 2003/0153953 A1 | 8/2003 | Park et al. | |
| 2003/0153955 A1 | 8/2003 | Park et al. | |
| 2003/0153956 A1 | 8/2003 | Park et al. | |
| 2003/0163059 A1 | 8/2003 | Poezevera et al. | |
| 2003/0171791 A1 | 9/2003 | KenKnight et al. | |
| 2003/0212445 A1 | 11/2003 | Weinberg | |
| 2004/0002741 A1 | 1/2004 | Weinberg | |
| 2004/0002742 A1 | 1/2004 | Florio | |
| 2004/0015103 A1 | 1/2004 | Aminian et al. | |
| 2004/0049132 A1 | 3/2004 | Barron et al. | |
| 2004/0102814 A1 | 5/2004 | Sorensen et al. | |
| 2004/0111040 A1 | 6/2004 | Ni et al. | |
| 2004/0111041 A1 | 6/2004 | Ni et al. | |
| 2005/0021103 A1 | 1/2005 | DiLorenzo | |
| 2005/0021104 A1 | 1/2005 | DiLorenzo | |
| 2005/0042589 A1 | 2/2005 | Hatlestad et al. | |
| 2005/0113710 A1 | 5/2005 | Stahmann et al. | |
| 2005/0119703 A1 | 6/2005 | DiLorenzo | |
| 2005/0177192 A1 | 8/2005 | Rezai et al. | |
| 2005/0215847 A1 | 9/2005 | Heruth et al. | |
| 2005/0222626 A1 | 10/2005 | DiLorenzo | |
| 2005/0240086 A1 | 10/2005 | Akay | |
| 2005/0240242 A1 | 10/2005 | DiLorenzo | |
| 2005/0245790 A1 | 11/2005 | Bergfalk et al. | |
| 2006/0224191 A1 | 10/2006 | DiLorenzo | |
| 2006/0293720 A1 | 12/2006 | DiLorenzo | |
| 2007/0038265 A1 | 2/2007 | Tcheng et al. | |
| 2007/0073355 A1 | 3/2007 | DiLorenzo | |
| 2007/0142862 A1 | 6/2007 | DiLorenzo | |
| 2007/0250121 A1 * | 10/2007 | Miesel et al. | 607/3 |
| 2007/0293737 A1 * | 12/2007 | Heruth et al. | 600/300 |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 | 5/1999 |
| WO | WO98/00197 | 1/1998 |
| WO | WO 99/013765 | 3/1999 |
| WO | WO 01/37930 | 5/2001 |
| WO | WO 2001/037930 | 5/2001 |
| WO | WO 02/28282 | 4/2002 |
| WO | WO 02/28282 A1 | 4/2002 |
| WO | WO 02/41771 A1 | 5/2002 |
| WO | WO 02/087433 | 11/2002 |
| WO | WO 2002/087433 | 11/2002 |
| WO | WO 02/096512 A1 | 12/2002 |
| WO | WO 02/100267 | 12/2002 |
| WO | WO 02/100267 A1 | 12/2002 |
| WO | WO 03/024325 | 3/2003 |
| WO | WO 03/051356 | 6/2003 |
| WO | WO 03/051356 A1 | 6/2003 |
| WO | WO 03/065891 A2 | 8/2003 |
| WO | WO 05/028029 | 3/2005 |
| WO | WO 05/035050 | 4/2005 |
| WO | WO 2005/035050 | 4/2005 |

OTHER PUBLICATIONS

"IBM & Citizen Watch develop Linux-based 'WatchPad'," 5 pgs., http://www.linuxdevices.com/news/NS6580187845.html, (2006).

Tuisku, Katinka, "Motor Activity Measured By Actometry in Neuropsychiatric Disorders," Department of Psychiatry, University of Helsinski, Helsinki, Finland, 115 pgs., (2002).

Kassam, M., "2005 EDP Topic 'MK4': Tremor Data-Logger for Parkinson's Disease Patients," http://www.ee.ryerson.ca/~courses/edp2005/MK4.html, 3 pgs., (2006).

"Design Competition: Runners-Up for the Best Three Designs," EPN, vol. 26, No. 1, (2002).

"MiniMitter® Physiological and Behavioral Monitoring for Humans and Animals," http://www.minimitter.com/Products/Actiwatch, 3 pgs., (2006).

Notification of Transmittal of the International Preliminary Report on Patentability for corresponding PCT Application Serial No. PCT/US2005/008800, dated Mar. 24, 2006, 18 pgs.

Invitation to Pay Additional Fees and Communication Relating to the Results of the Partial International Search for PCT/US2005/008800, dated Jun. 28, 2005 (9 pgs.).

M.T. Smith et al, "Presleep Cognitions in Patients with Insomnia Secondary to Chronic Pain", Journal of Behavioral Medicine, vol. 24, No. 1, 2001.

Michael T. Smith et al., "How do sleep disturbance and chronic pain inter-relate? Insights from the longitudinal and cognitive-bahavioral clinical trials literature", Sleep Medicines Reviews, YSMRV 286-19/6/2003.

Suanne Goodrich et al., "The Predictions of Pain Using Measures of Sleep Quality", Pain Digest (1998) 8:23-25.

"Analysis of heart rate dynamics by methods derived from nonlinear mathematics: Clinical applicability and prognostic significance" http:/herkules.oulu.fi.isbn9514250133/html/x222.html (2004).

U.S. Appl. No. 10/826,925, entitled Collecting Sleep Quality Information via a Medical Device, filed Apr. 15, 2004.

U.S. Appl. No. 10/825,953, entitled "Controlling Therapy Based on Sleep Quality", filed Apr. 15, 2004.

U.S. Appl. No. 10/825,955, entitled "Collecting Activity and Sleep Quality Information via a Medical Device", filed Apr. 15, 2004.

U.S. Appl. No. 10/825,964, entitled "Detecting Sleep", filed Apr. 15, 2004.

U.S. Appl. No. 10/826,926, entitled "Collecting Posture Information to Evaluate Therapy", filed Apr. 15, 2004.

U.S. Appl. No. 11/081,873, entitled "Sensitivity Analysis for Selecting Therapy Parameter Sets", filed Mar. 16, 2005.

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiolgy Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare - A Global Leader in Sleep Diagnostics, Embletta Recording System, http://www.medcare.com/products/diagnostic/embletta/, 2 pgs. Jan. 31, 2005.

Medcare - A Global Leader in Sleep Diagnostics, Somnologica for Embletta. http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/cmsall/70564A3FCBE4188AC1256EF4.., 4 pgs. Jan. 31, 2005.

Merlin, http://www.aha.ru/~pir/english/merlin/, 4 pags. Jan. 31, 2005.

Sleep Solutions - PR Newswire: Sleep Solutions Introduces NovaSom™ QSG™ for PSG.., http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://www.quietsleep.com/snoringagapnea/sleepstrip.htm, 8 pgs. Jan. 31, 2005.

"Bitestrip Flier,"downloaded from the Internet Archive of www.quietsleep.com dated Jan. 29, 2005 http://archive.org/web/20041124080003/www.quietsleep.com/pdf/Bitestrip+Flier,pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism,"downloaded from Internet Archive of www.quietsleep.com dated Jan. 29, 2005 http://web.archive.org/web/20041124072922/www.quietsleep.com/pdf/BiteStrip-+Novel+Screener.pdf.

European Search Report dated Oct. 2, 2007 for European Patent Application Serial No. 53.92643/01 (6 pgs.).

* cited by examiner

COLLECTING ACTIVITY INFORMATION TO EVALUATE THERAPY

This application claims the benefit of U.S. Provisional Application No. 60/553,778, filed Mar. 16, 2004, which is incorporated herein by reference in its entirety.

TECHNICAL FIELD

The invention relates to medical devices and, more particularly, to medical devices that deliver therapy.

BACKGROUND

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders and congestive heart failure.

In some cases, these ailments are treated via a medical device, such as an implantable medical device (IMD). For example, patients may receive an implantable neurostimulator or drug delivery device to treat chronic pain or a movement disorder. Congestive heart failure may be treated by, for example, a cardiac pacemaker.

SUMMARY

In general, the invention is directed to techniques for evaluating a therapy delivered to a patient by a medical device based on patient activity. At any given time, the medical device delivers the therapy according to a current set of therapy parameters. The therapy parameters may change over time such that the therapy is delivered according to a plurality of different therapy parameter sets. The medical device periodically determines an activity level of the patient, and associates each determined activity level with the current therapy parameter set. A value of at least one activity metric is determined for each of the therapy parameter sets based on the activity levels associated with that parameter set. A list of the therapy parameter sets and associated activity metrics is presented to a user, such as a clinician, for evaluation of the relative efficacy of the therapy parameter sets. The list may be ordered according to the activity metric values to aid in evaluation of the therapy parameter sets. In this manner, the user may readily identify the therapy parameter sets that support the highest activity levels for the patient, and evaluate the relative efficacy of the parameter sets.

The medical device monitors at least one signal that is generated by a sensor and varies as a function of patient activity. For example, the medical device may monitor a signal generated by an accelerometer, a bonded piezoelectric crystal, a mercury switch, or a gyro. In some embodiments, the medical device may monitor a signal that indicates a physiological parameter of the patient, which in turn varies as a function of patient activity. For example, the medical device may monitor a signal that indicates the heart rate, respiration rate, respiratory volume, core temperature, or muscular activity of the patient.

The medical device may periodically determine an activity level of the patient based on the one or more signals. In some embodiments, the medical device periodically determines a number of activity counts based on the signals, and the number of activity counts is stored as the activity level. The number of activity counts may be a number of threshold crossings by a signal generated by a sensor such as an accelerometer or piezoelectric crystal during a sample period, or a number of switch contacts indicated by the signal generated by a sensor such as mercury switch during a sample period.

In some embodiments, the medical device may periodically determine a heart rate, respiration rate, respiratory volume, core temperature, and/or muscular activity level of the patient based on one or more signals. The determined values of these parameters may be mean or median values. The medical device may compare a determined value of such a physiological parameter to one or more thresholds to determine a number of activity counts, which may be stored as a determined activity level. In other embodiments, the medical device may store the determined physiological parameter value as a determined activity level.

The use of activity counts, however, may allow the medical device to determine an activity level based on a plurality of signals. For example, the medical device may determine a first number of activity counts based on an accelerometer signal and a second number of activity counts based on a heart rate determined at the time the accelerometer signal was sampled. The medical device may determine an activity level by calculating the sum or average, which may be a weighted sum or average, of first and second activity counts.

As mentioned above, the medical device may associate each determined activity level with a current set of therapy parameters and, for each of a plurality of therapy parameter sets used by the medical device over time, a value of one or more activity metrics is determined. An activity metric value may be, for example, a mean or median activity level, such as an average number of activity counts per unit time. In other embodiments, an activity metric value may be chosen from a predetermined scale of activity metric values based on comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set. One or both of the medical device or a programming device may determine the activity metric values as described herein.

The programming device or, in some external medical device embodiments, the medical device, presents a list of the plurality of parameter sets and associated activity metric values via a display. The programming device may order the list according to the activity metric values. Where values are determined for a plurality of activity metrics for each of the therapy parameter sets, the programming device may order the list according to the values of a user selected one of the activity metrics. The programming device may also present other activity information to a user, such as a trend diagram of activity over time, or a histogram or pie chart illustrating percentages of time that activity levels were within certain ranges. The programming device may generate such charts or diagrams using activity levels associated with a particular one of the therapy parameter sets, or all of the activity levels determined by the medical device.

In one embodiment, the invention is directed to a method in which a signal that varies as a function of patient activity is monitored, and an activity level of the patient is periodically determined based on the signal. Each of the determined activity levels is associated with a therapy parameter set currently used by a medical device to deliver therapy to the patient when the activity level is determined, and a value of an activity metric is determined for each of a plurality of therapy parameter sets based on activity levels associated with the therapy parameter sets.

In another embodiment, the invention is directed to a medical system comprising a medical device that delivers a therapy to a patient and a processor. The processor monitors a signal that varies as a function of patient activity, periodically determines an activity level of the patient based on the signal, associates each of the determined activity levels with a therapy parameter set currently used by the medical device to deliver the therapy to the patient when the activity level is determined, and determines a value of an activity metric for each of a plurality of therapy parameter sets based on activity levels associated with the therapy parameter sets.

In another embodiment, the invention is directed to a medical system comprising means for monitoring a signal that varies as a function of patient activity via a medical device that delivers a therapy to a patient, means for periodically determining an activity level of the patient based on the signal, means for associating each of the determined activity levels with a current therapy parameter set, means for determining a value of an activity metric for each of a plurality of therapy parameter sets based on activity levels associated with the therapy parameter sets, and means for presenting a list of the plurality of therapy parameter sets and activity metric values associated with the therapy parameter sets.

In another embodiment, the invention is directed to a medical system comprising an implantable medical device and an external programming device including a display. The implantable medical device delivers a therapy to a patient, monitors a signal that varies as a function of patient activity, periodically determines an activity level of the patient based on the signal, and associates each of the determined activity levels with a current therapy parameter set. The external programming device receives information identifying a plurality of therapy parameter sets and associated activity levels from the implantable medical device via telemetry, determines a value of an activity metric for each of a plurality of therapy parameter sets based on activity levels associated with the therapy parameter sets, and presents a list of the plurality of therapy parameter sets and activity metric values associated with the therapy parameter sets via the display.

In another embodiment the invention is directed to a programming device comprising a telemetry circuit, a user interface including a display, and a processor. The processor receives information identifying a plurality of therapy parameter sets and associated activity levels from an implantable medical device via the telemetry circuit, determines a value of an activity metric for each of a plurality of therapy parameter sets based on activity levels associated with the therapy parameter sets, and presents a list of the plurality of therapy parameter sets and activity metric values associated with the therapy parameter sets via the display.

In another embodiment, the invention is directed to a computer-readable medium comprising program instructions. The program instructions cause a programmable processor to receive information identifying a plurality of therapy parameter sets and associated activity levels from an implantable medical device, determine a value of an activity metric for each of a plurality of therapy parameter sets based on activity levels associated with the therapy parameter sets, and present a list of the plurality of therapy parameter sets and activity metric values associated with the therapy parameter sets.

The invention is capable of providing one or more advantages. For example, a medical system according to the invention may provide a clinician with an objective indication of the efficacy different sets of therapy parameters. Further, by displaying therapy parameter sets and associated activity metric values in an ordered and, in some cases, sortable list, the medical system may allow the clinician to more easily compare the relative efficacies of a plurality of therapy parameter sets. The medical system may be particularly useful in the context of trial neurostimulation for treatment of chronic pain, where the patient is encouraged to try a plurality of therapy parameter sets to allow the patient and clinician to identify efficacious therapy parameter sets.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
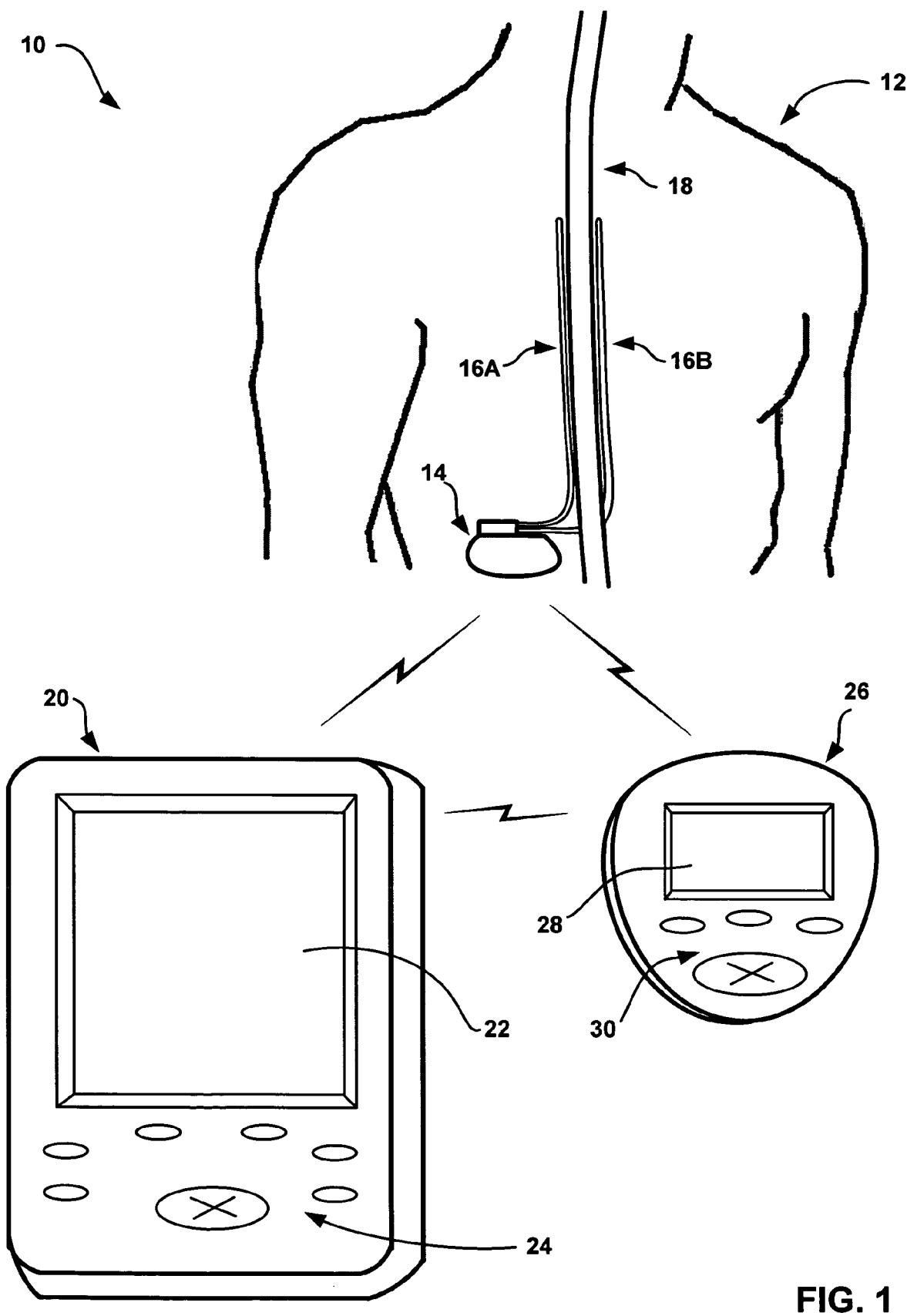
FIG. 1 is a conceptual diagram illustrating an example system that includes an implantable medical device that collects activity information according to the invention.

FIG. 1 is a conceptual diagram illustrating an example system 10 that includes an implantable medical device (IMD) 14 that collects information relating to the activity of a patient 12. In the illustrated example system 10, IMD 14 takes the form of an implantable neurostimulator that delivers neurostimulation therapy in the form of electrical pulses to patient 12. However, the invention is not limited to implementation via an implantable neurostimulator. For example, in some embodiments of the invention, IMD 14 may take the form of an implantable pump or implantable cardiac rhythm management device, such as a pacemaker, that collects activity information. Further, the invention is not limited to implementation via an IMD. In other words, any implantable or external medical device may collect activity information according to the invention.

In the illustrated example, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence, sexual dysfunction, or gastroparesis.

IMD 14 delivers therapy according to a set of therapy parameters, i.e., a set of values for a number of parameters that define the therapy delivered according to that therapy parameter set. In embodiments where IMD 14 delivers neurostimulation therapy in the form of electrical pulses, the parameters for each therapy parameter set may include voltage or current pulse amplitudes, pulse widths, pulse rates, duration, duty cycle and the like. Further, each of leads 16 includes electrodes (not shown in FIG. 1), and a therapy parameter set may include information identifying which electrodes have been selected for delivery of pulses, and the polarities of the selected electrodes. Therapy parameter sets used by IMD 14 may include a number of parameter sets programmed by a clinician (not shown), and parameter sets representing adjustments made by patient 12 to these preprogrammed sets.

System 10 also includes a clinician programmer 20. The clinician may use clinician programmer 20 to program therapy for patient 12, e.g., specify a number of therapy parameter sets and provide the parameter sets to IMD 14. The clinician may also use clinician programmer 20 to retrieve information collected by IMD 14. The clinician may use clinician programmer 20 to communicate with IMD 14 both during initial programming of IMD 14, and for collection of information and further programming during follow-up visits.

Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus, mouse, or the like.

Clinician and patient programmers 20, 26 are not limited to the hand-held computer embodiments illustrated in FIG. 1. Programmers 20, 26 according to the invention may be any sort of computing device. For example, a programmer 20, 26 according to the invention may be a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 collects patient activity information. Specifically, as will be described in greater detail below, IMD 14 may periodically determine an activity level of patient 12 based on a signal that varies as a function of patient activity. IMD 14 may associate each determined activity level with the therapy parameter set that is currently active when the activity level is determined. An activity level may comprise, for example, a number of activity counts, or a value for a physiological parameter that reflects patient activity.

Over time, IMD 14 uses a plurality of therapy parameter sets to deliver the therapy to patient 12. A processor within IMD 14, clinician programmer 20, or patient programmer 26 determines a value of one or more activity metrics for each of the plurality of therapy parameter sets based on the activity levels associated with the therapy parameter sets. An activity metric value may be, for example, a mean or median activity level, such as an average number of activity counts per unit time. In other embodiments, an activity metric value may be chosen from a predetermined scale of activity metric values based on a comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set.

In some embodiments, a plurality of activity metric values are determined for each of the plurality of therapy parameter sets. In such embodiments, an overall activity metric value may be determined. For example, the plurality of individual activity metric values may be used as indices to identify an overall activity metric value from a look-up table. The overall activity metric may selected from a predetermined scale of activity metric values, which may be numeric, such as activity metric values from 1-10, or qualitative, such as low, medium or high activity.

One or more of IMD 14, clinician programmer 20, and patient programmer 26 may determine the activity metric values as described herein. In some embodiments, IMD 14 determines and stores activity metric values for each of a plurality of therapy parameter sets, and provides information identifying the therapy parameter sets and the associated activity metric values to clinician programmer 20. In other embodiments, IMD 14 provides information identifying the therapy parameter sets and associated activity levels to clinician programmer 20, and clinician programmer 20 determines the activity metric values for each of the therapy parameter sets.

In either of these embodiments, clinician programmer 20 presents a list of the plurality of parameter sets and associated activity metric values to the clinician via display 22. Programmer 20 may order the list according to the activity metric values. Where values are determined for a plurality of activity metrics for each of the therapy parameter sets, programmer 20 may order the list according to the values of one of the activity metrics that is selected by the clinician. Programmer 20 may also present other activity information to the clinician, such as a trend diagram of activity over time, or a histogram or pie chart illustrating percentages of time that activity levels were within certain ranges. Programmer 20 may generate such charts or diagrams using activity levels associated with a particular one of the therapy parameter sets, or all of the activity levels determined by IMD 14.

However, the invention is not limited to embodiments that include programmer 20, or embodiments in which programmer 20 presents activity information to the clinician. For example, in some embodiments, an external medical device comprises a display. In such embodiments, the external medical device both determines the activity metric values for the plurality of therapy parameter sets, and presents the list of therapy parameter sets and activity metric values.

Further, the invention is not limited to embodiments in which a medical device determines activity levels. For example, in some embodiments, IMD 14 may instead periodically record samples of one or more signals that vary as a function of patient activity, and associated the samples with a current therapy parameter set. In such embodiments, programmer 20 may receive information identifying a plurality of therapy parameter sets and the samples associated with the parameter sets, may determine activity levels based on the samples, and may determine one or more activity metric values for each of the therapy parameter sets based on the determined activity levels.

Figure 2:
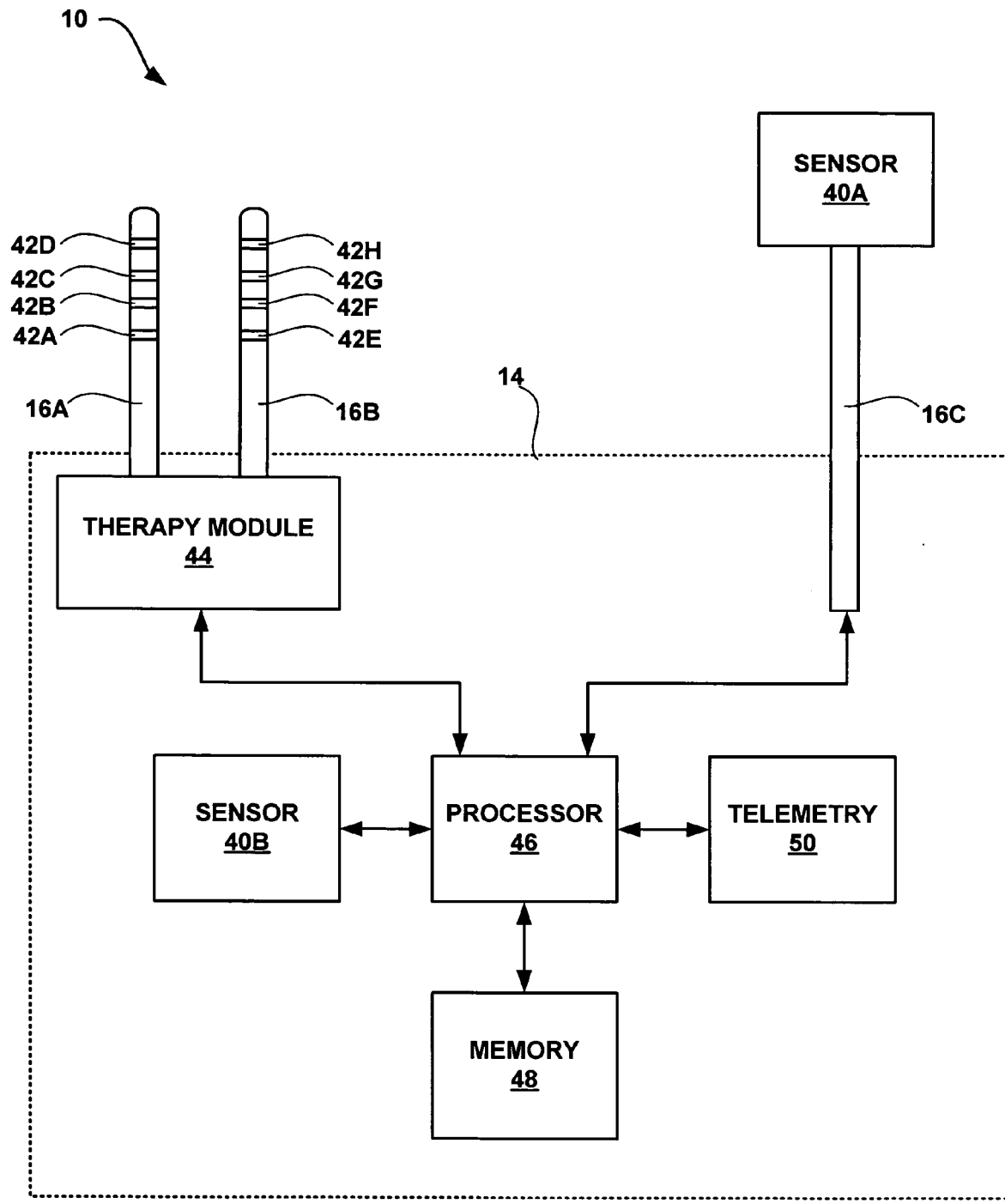
FIG. 2 is a block diagram further illustrating the example system and implantable medical device of FIG. 1.

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that generate signals that vary as a function of patient activity. As will be described in greater detail below, IMD 14 monitors the signals, and may periodically determine an activity level based on the signals.

IMD 14 may deliver neurostimulation therapy via electrodes 42A-D of lead 16A and electrodes 42E-H of lead 16B (collectively "electrodes 42"). Electrodes 42 may be ring electrodes. The configuration, type and number of electrodes 42 illustrated in FIG. 2 are merely exemplary. For example, leads 16A and 16B may each include eight electrodes 42, and the electrodes 42 need not be arranged linearly on each of leads 16A and 16B.

Electrodes 42 are electrically coupled to a therapy delivery module 44 via leads 16A and 16B. Therapy delivery module 44 may, for example, include an output pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal that varies as a function of patient activity. IMD 14 may include circuitry (not shown) that conditions the signals generated by sensors 40 such that they may be analyzed by processor 46. For example, IMD 14 may include one or more analog to digital converters to convert analog signals generated by sensors 40 into digital signals usable by processor 46, as well as suitable filter and amplifier circuitry. Although shown as including two sensors 40, system 10 may include any number of sensors.

Further, as illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor 40 located outside of IMD 14 may be in wireless communication with processor 46.

A sensor 40 may be, for example, an accelerometer, a bonded piezoelectric crystal, a mercury switch, or a gyro. Processor 46 may determine an activity level based on a signal generated by one of these types of sensors 40 by sampling the signal and determining a number of activity counts during the sample period. Processor 46 may then store the determined number of activity counts in memory 48 as an activity level.

For example, processor 46 may compare the sample of a signal generated by an accelerometer or piezoelectric crystal to one or more amplitude thresholds stored within memory 48. Processor 46 may identify each threshold crossing as an activity count. Where processor 46 compares the sample to multiple thresholds with varying amplitudes, processor 46 may identify crossing of higher amplitude thresholds as multiple activity counts. Using multiple thresholds to identify activity counts, processor 46 may be able to more accurately determine the extent of patient activity for both high impact, low frequency and low impact, high frequency activities. In embodiments in which a sensor 40 takes the form of a mercury switch, processor 46 may identify the number of switch contacts indicated during the sample period as the number of activity counts.

In embodiments in which a sensor 40 comprises an accelerometer or piezoelectric crystal, IMD 14 may include a filter (not shown), or processor 46 may apply a digital filter, that passes a band from approximately 0.1 Hz to 10 Hz. The filter may reduce noise in the signal, and pass the portion of the signal that reflects patient activity.

In some embodiments, processor 46 may monitor a signal that indicates a physiological parameter of patient 12, which in turn varies as a function of patient activity. For example, processor 46 may monitor a signal that indicates the heart rate, respiration rate, respiratory volume, core temperature, or muscular activity of the patient. In such embodiments, processor 46 may periodically determine the heart rate, respiration rate, respiratory volume, core temperature, or muscular activity level of patient 12 based on the signal. The determined values of these parameters may be mean or median values.

Sensors 40 may include electrodes located on leads 16 or integrated as part of the housing of IMD 14 that generates an electrogram signal as a function of electrical activity of the heart of patient 12, and processor 46 may periodically determine the heart rate of patient 12 based on the electrogram signal. In other embodiments, a sensor 40 may include an acoustic sensor within IMD 14, a pressure sensor within the bloodstream or cerebrospinal fluid of patient 12, or a temperature sensor located within the bloodstream of patient 12. The signals generated by such sensors 40 may vary as a function of contraction of the heart of patient 12, and can be used by processor 46 to periodically determine the heart rate of patient 12.

In some embodiments, sensors 40 may include an electrode pair, including one electrode integrated with the housing of IMD 14 and one of electrodes 42, that generates a signal as a function of the thoracic impedance of patient 12, which varies as a function of respiration by patient 12. In other embodiments, sensors 40 may include a strain gauge, bonded piezoelectric element, or pressure sensor within the blood or cerebrospinal fluid that generates a signal that varies based on patient respiration. Processor 46 may monitor the signals generated by such sensors 40 to periodically determine a respiration rate and/or respiratory volume of patient 12. An electrogram generated by electrodes as discussed above may also be modulated by patient respiration, and processor 46 may use the electrogram as an indirect representation of respiration rate. Additionally, sensors 40 may include electrodes that generate an electromyogram (EMG) signal as a function of muscle electrical activity, or may include any of a variety of known temperature sensors to generate a signal as a function of a core temperature of patient 12. Such electrodes and temperature sensors may be incorporated within the housing of IMD 14, or coupled to IMD 14 via leads.

In some embodiments, processor 46 compares a determined value of such a physiological parameter to one or more thresholds or a look-up table stored in memory to determine a number of activity counts, and stores the determined number of activity counts in memory 48 as a determined activity level. In other embodiments, processor 46 may store the determined physiological parameter value as a determined activity level. The use of activity counts, however, may allow processor 46 to determine an activity level based on a plurality of signals generated by a plurality of sensors 40. For example, processor 46 may determine a first number of activity counts based on a sample of an accelerometer signal and a second number of activity counts based on a heart rate determined from an electrogram signal at the time the accelerometer signal was sampled. Processor 46 may determine an activity level by calculating the sum or average, which may be a weighted sum or average, of first and second activity counts.

Processor 46 may record activity levels continuously or periodically, e.g., one sample every minute or continuously for ten minutes each hour. In some embodiments, processor 46 limits recording of activity levels to relevant time periods, i.e., when patient 12 is awake or likely to be awake, and therefore likely to be active. For example, patient may indicate via patient programmer 26 when patient is going to sleep or awake. Processor 46 may receive these indications via a telemetry circuit 50 of IMD 14, and may suspend or resume recording of activity levels based on the indications. In other embodiments, processor 46 may maintain a real-time clock, and may record activity levels based on the time of day indicated by the clock, e.g., processor 46 may limit activity level recording to daytime hours.

In some embodiments, processor 46 may monitor one or more physiological parameters of patient 12 via signals generated by sensors 40, and may determine when patient 12 is attempting to sleep or asleep based on the physiological parameters. For example, processor 46 may determine when patient 12 is attempting to sleep by receiving an indication from patient programmer 26, or by monitoring the posture of patient 12 to determine when patient 12 is recumbent. Sensors 40 may include a plurality of orthogonally arranged accelerometers, and processor 46 may monitor the DC components of the signals generated by the accelerometers to determine when patient is recumbent.

In other embodiments, processor 46 determines when patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluidbodily fluid F, and estimate the time that patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that patient 12 is attempting to fall asleep as the time that the threshold is exceeded, or some amount of time after the threshold is exceeded. Any of a variety of combinations or variations of the above-described techniques may be used to determine when patient 12 is attempting to fall asleep, and a specific one or more techniques may be selected based on the sleeping and activity habits of a particular patient.

In order to determine whether patient 12 is asleep, processor 46 may monitor any one or more physiological parameters that discernibly change when patient 12 falls asleep, such as activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. Processor 46 may additionally or alternatively monitor the variability of one or more of these physiological parameters, such as heart rate and respiration rate, which may discernible change when patient 12 is asleep. Further details regarding monitoring physiological parameters to identify when a patient is attempting to sleep and when the patient is asleep may be found in a commonly-assigned and co-pending U.S. patent application Ser. No. 10/825,964 by Kenneth Heruth and Keith Miesel, entitled "DETECTING SLEEP," and filed Apr. 15, 2004, and is incorporated herein by reference in its entirety.

In other embodiments, processor 46 may record activity levels in response to receiving an indication from patient 12 via patient programmer 26. For example, processor 46 may record activity levels during times when patient 12 believes the therapy delivered by IMD 14 is ineffective and/or the symptoms experienced by patient 12 have worsened. In this manner, processor 46 may limit data collection to periods in which more probative data is likely to be collected, and thereby conserve a battery and/or storage space within memory 48.

Further, as described above, the invention is not limited to embodiments in which IMD 14 determines activity levels. In some embodiments, processor 46 may periodically store samples of the signals generated by sensors 40 in memory 48, rather than activity levels, and may associate those samples with the current therapy parameter set.

Figure 3:
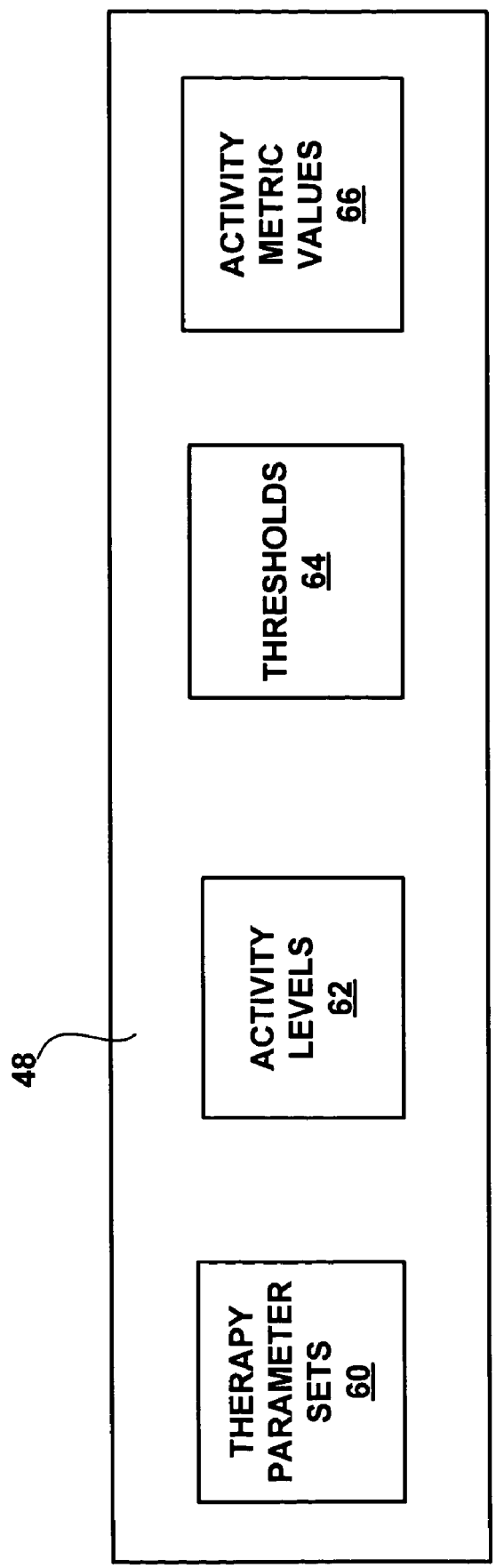
FIG. 3 is a block diagram illustrating an example memory of the implantable medical device of FIG. 1.

FIG. 3 illustrates memory 48 of IMD 14 in greater detail. As shown in FIG. 3, memory 48 stores information describing a plurality of therapy parameter sets 60. Therapy parameter sets 60 may include parameter sets specified by a clinician using clinician programmer 20. Therapy parameter sets 60 may also include parameter sets that are the result of patient 12 changing one or more parameters of one of the preprogrammed therapy parameter sets. For example, patient 12 may change parameters such as pulse amplitude, frequency or pulse width via patient programmer 26.

Memory 48 also stores the activity levels 62 determined by processor 46. When processor 46 determines an activity level as discussed above, processor 46 associates the determined activity level with the current one of therapy parameter sets 60, e.g., the one of therapy parameter sets 60 that processor 46 is currently using to control delivery of therapy by therapy module 44 to patient 12. For example, processor 46 may store determined activity levels 62 within memory 48 with an indication of the parameter sets 60 with which they are associated. In other embodiments, processor 46 stores samples (not shown) of signals generated by sensors 40 within memory 48 with an indication of the parameter sets 60 with which they are associated.

In some embodiments, processor 46 determines a value of one or more activity metrics for each of therapy parameter sets 60 based on the activity levels 62 associated with the parameter sets 60. Processor 46 may store the determined activity metric values 66 within memory 48 with an indication as to which of therapy parameter sets 60 the determined values are associated with. For example, processor 46 may determine a mean or median of activity levels associated with a therapy parameter set, and store the mean or median activity level as an activity metric value 66 for the therapy parameter set.

In embodiments in which activity levels 62 comprise activity counts, processor 46 may store, for example, an average number of activity counts per unit time as an activity metric value. An average number of activity counts over a some period substantially between ten and sixty minutes, for example, may provide a more accurate indication of activity than an average over shorter periods by ameliorating the effect of transient activities on an activity signal or physiological parameters. For example, rolling over in bed may briefly increase the amplitude of an activity signal and a heart rate, thereby confounding the activity analysis.

In other embodiments, processor 46 may compare a mean or median activity level to one or more threshold values 64, and may select an activity metric value from a predetermined scale of activity metric values based on the comparison. The scale may be numeric, such as activity metric values from 1-10, or qualitative, such as low, medium or high activity. The scale of activity metric values may be, for example, stored as a look-up table within memory 48. Processor 46 stores the activity metric value 66 selected from the scale within memory 48.

In some embodiments, processor 46 compares each activity level 62 associated with a therapy parameter set 60 to one or more threshold values 64. Based on the comparison, processor 46 may determine percentages of time above and/or below the thresholds, or within threshold ranges. Processor 46 may store the one or more determined percentages within memory 48 as one or more activity metric values 66 for that therapy parameter set. In other embodiments, processor 46 compares each activity level 62 associated with a therapy parameter set 66 to a threshold values 64, and determines an average length of time that consecutively recorded activity levels 62 remained above the threshold as an activity metric value 66 for that therapy parameter set.

In some embodiments, processor 46 determines a plurality of activity metric values for each of the plurality of therapy parameter sets, and determines an overall activity metric value for a parameter set based on the values of the individual activity metrics for that parameter set. For example, processor 46 may use the plurality of individual activity metric values as indices to identify an overall activity metric value from a look-up table stored in memory 48. Processor 46 may select the overall metric value from a predetermined scale of activity metric values, which may be numeric, such as activity metric values from 1-10, or qualitative, such as low, medium or high activity.

As shown in FIG. 2, IMD 14 includes a telemetry circuit 50, and processor 46 communicates with programmers 20, 26 via telemetry circuit 50. In some embodiments, processor 46 provides information identifying therapy parameter sets 60 and activity metric values 66 associated with the parameter sets to programmer 20, and programmer 20 displays a list of therapy parameter sets 60 and associated activity metric values 66. In other embodiments, as will be described in greater detail below, processor 46 does not determine activity metric values 66. Instead, processor 46 provides activity levels 62 to programmer 20 via telemetry circuit 50, and programmer 20 determines activity metric values 66 for display to the clinician. Further, in other embodiments, processor 46 provides samples of signals generated by sensors 40 to programmer 20 via telemetry circuit 50, and programmer 20 may both determine activity levels 62 and activity metric values 66 based on the samples. Some external medical device embodiments of the invention include a display, and a processor of such an external medical device may both determine activity metric values 66 and display a list of therapy parameter sets 60 and associated activity metric values 66 to a clinician.

Figure 4:
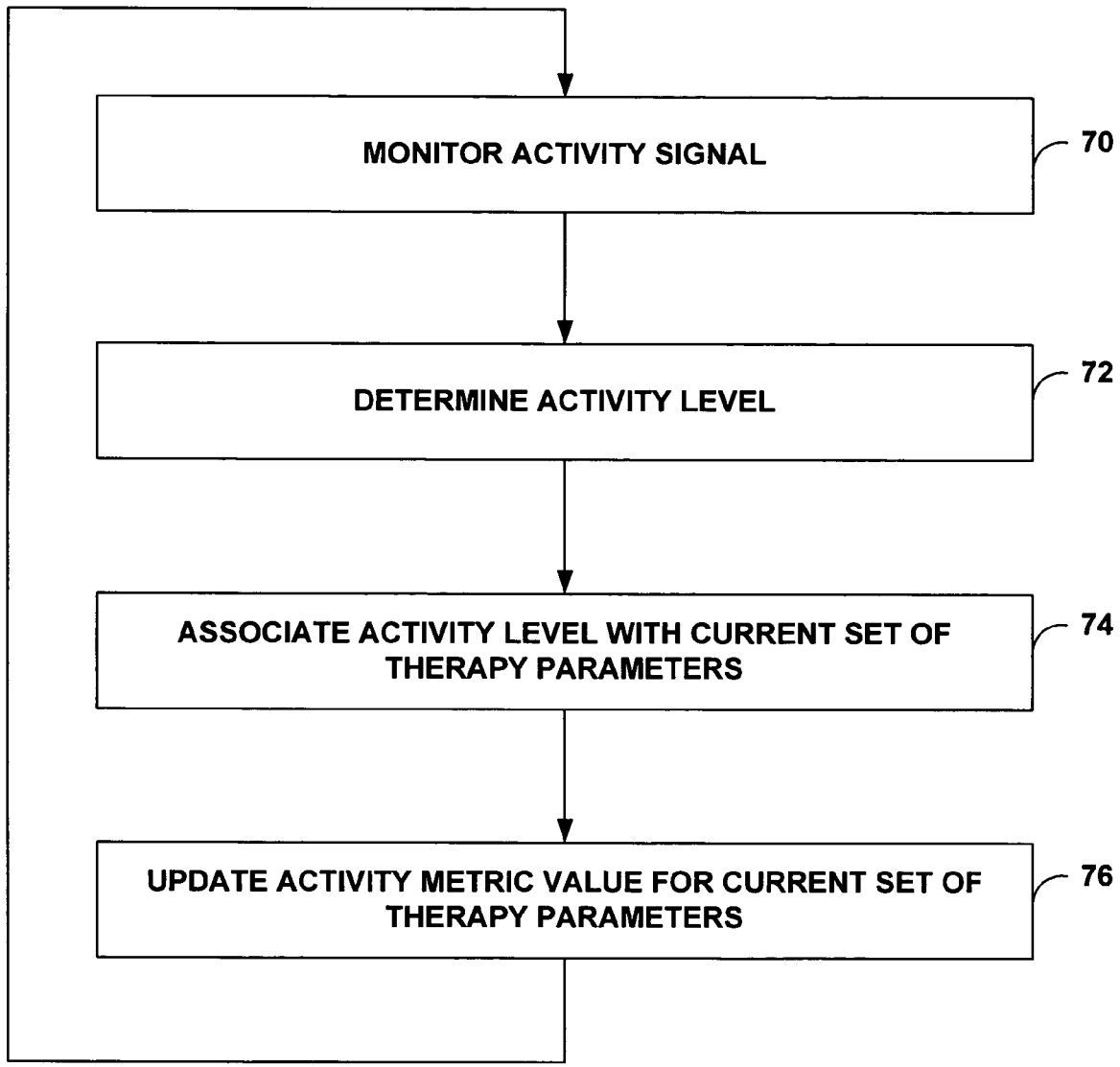
FIG. 4 is a flow diagram illustrating an example method for collecting activity information that may be employed by an implantable medical device.

FIG. 4 is a flow diagram illustrating an example method for collecting activity information that may be employed by IMD 14. IMD 14 monitors one or more activity signals (70). For example, IMD 14 may monitor a signal generated by an accelerometer or piezoelectric crystal, and/or a signal that indicates a physiological parameter that varies as a function of patient activity, such heart rate, respiration rate, respiratory volume, core temperature, or muscle activity.

IMD 14 determines an activity level 62 (72). For example, IMD 14 may determine a number of activity counts based on the one or more signals, as described above. IMD 14 identifies the current therapy parameter set 60, and associates the determined activity level 62 with the current therapy parameter set 60 (74). For example, IMD 14 may store the determined activity level 62 in memory 48 with an indication of the current therapy parameter set 60. IMD 14 may then update one or more activity metric values 66 associated with the current therapy parameter set 60, as described above (76).

IMD 14 may periodically perform the example method illustrated in FIG. 4, e.g., may periodically monitor the activity signal (70), determine activity levels 62 (72), and associate the determined activity levels 62 with a current therapy parameter set 60 (74). As described above, IMD 14 may only perform the example method during daytime hours, or when patient is awake and not attempting to sleep, and/or only in response to an indication received from patient 12 via patient programmer 20. IMD 14 need not update activity metric values 66 each time an activity level 62 is determined. In some embodiments, for example, IMD 14 may store activity levels 62 within memory, and may determine the activity metric values 66 upon receiving a request for the values from clinician programmer 20.

Further, in some embodiments, as will be described in greater detail below, IMD 14 does not determine the activity metric values 66, but instead provides activity levels 62 to a programming device, such as clinician programmer 20 or patient programmer 26. In such embodiments, the programming device determines the activity metric values 66 associated with each of the therapy parameter sets 60. Additionally, as described above, IMD 14 need not determine activity levels 62, but may instead store samples of the signals generated by sensors 40. In such embodiments, the programming device may determine both activity levels 62 and activity metric values 66 based on the samples.

Figure 5:
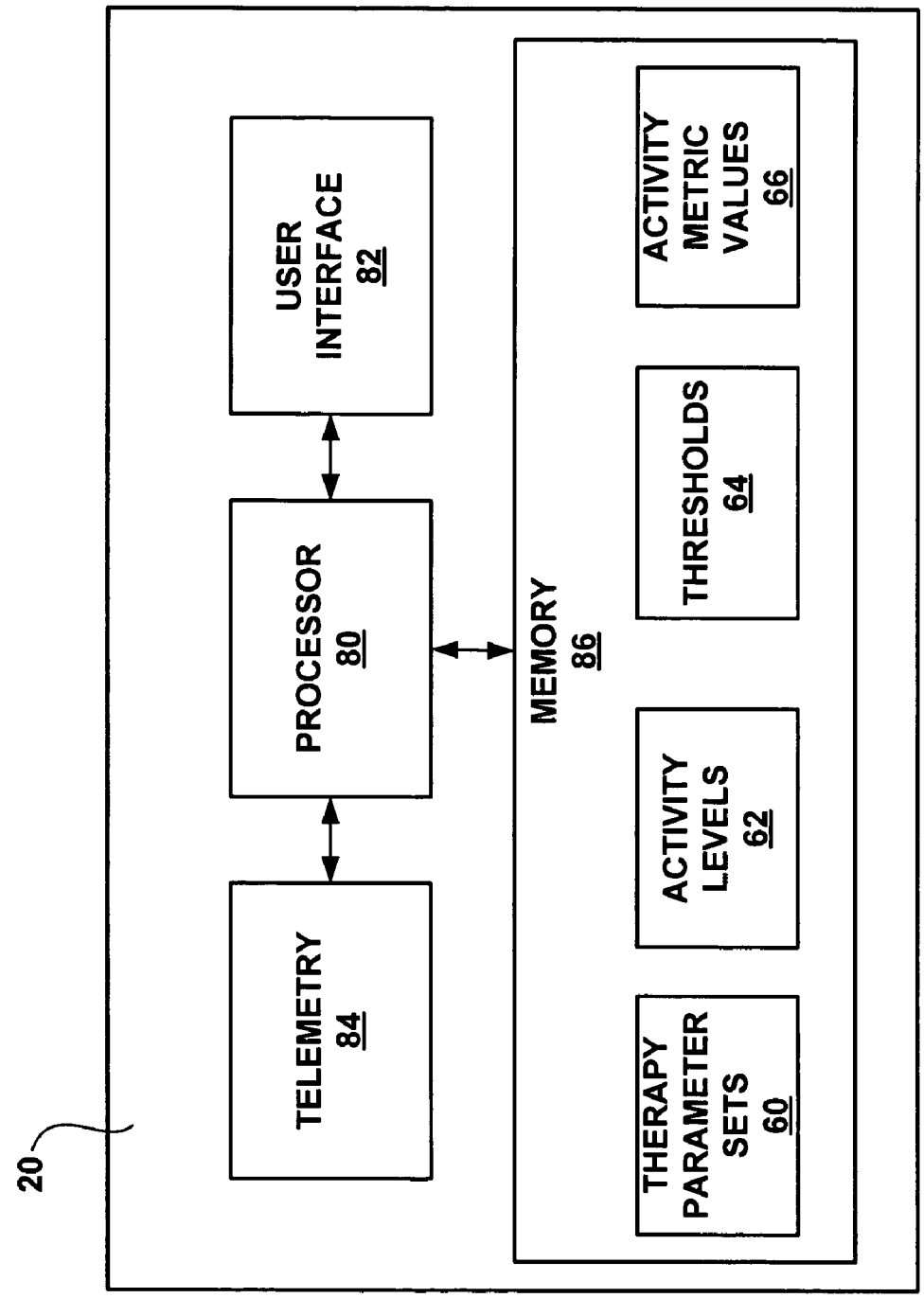
FIG. 5 is a block diagram illustrating an example clinician programmer.

FIG. 5 is a block diagram illustrating clinician programmer 20. A clinician may interact with a processor 80 via a user interface 82 in order to program therapy for patient 12, e.g., specify therapy parameter sets. Processor 80 may provide the specified therapy parameter sets to IMD 14 via telemetry circuit 84.

At another time, e.g., during a follow up visit, processor 80 may receive information identifying a plurality of therapy parameter sets 60 from IMD 14 via telemetry circuit 84, which may be stored in a memory 86. The therapy parameter sets 60 may include the originally specified parameter sets, and parameter sets resulting from manipulation of one or more therapy parameters by patient 12 using patient programmer 26. In some embodiments, processor 80 also receives activity metric values 66 associated with the therapy parameter sets 60, and stores the activity metric values in memory 86.

In other embodiments, processor 80 receives activity levels 62 associated with the therapy parameter sets 60, and determines values 66 of one or more activity metrics for each of the plurality of therapy parameter sets 60 using any of the techniques described above with reference to IMD 14 and FIGS. 2 and 3. Processor 80 may, for example, use threshold values 64 stored in memory 86 to determine activity metric values 66, as described above. In still other embodiments, processor 80 receives samples of activity signals from IMD 14, and determines activity levels 62 and activity metric values 66 based on signals using any of the techniques described above with reference to IMD 14 and FIGS. 2 and 3.

Upon receiving or determining activity metric values 66, processor 80 generates a list of the therapy parameter sets 60 and associated activity metric values 66, and presents the list to the clinician. User interface 82 may include display 22, and processor 80 may display the list via display 22. The list of therapy parameter sets 60 may be ordered according to the associated activity metric values 66. Where a plurality of activity metric values are associated with each of the parameter sets, the list may be ordered according to the values of the activity metric selected by the clinician. Processor 80 may also present other activity information to a user, such as a trend diagram of activity over time, or a histogram, pie chart, or other illustration of percentages of time that activity levels 62 were within certain ranges. Processor 80 may generate such charts or diagrams using activity levels 62 associated with a particular one of the therapy parameter sets 66, or all of the activity levels 62 recorded by IMD 14.

User interface 82 may include display 22 and keypad 24, and may also include a touch screen or peripheral pointing devices as described above. Processor 80 may include a microprocessor, a controller, a DSP, an ASIC, an FPGA, discrete logic circuitry, or the like. Memory 86 may include program instructions that, when executed by processor 80, cause clinician programmer 20 to perform the functions ascribed to clinician programmer 20 herein. Memory 86 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 6:
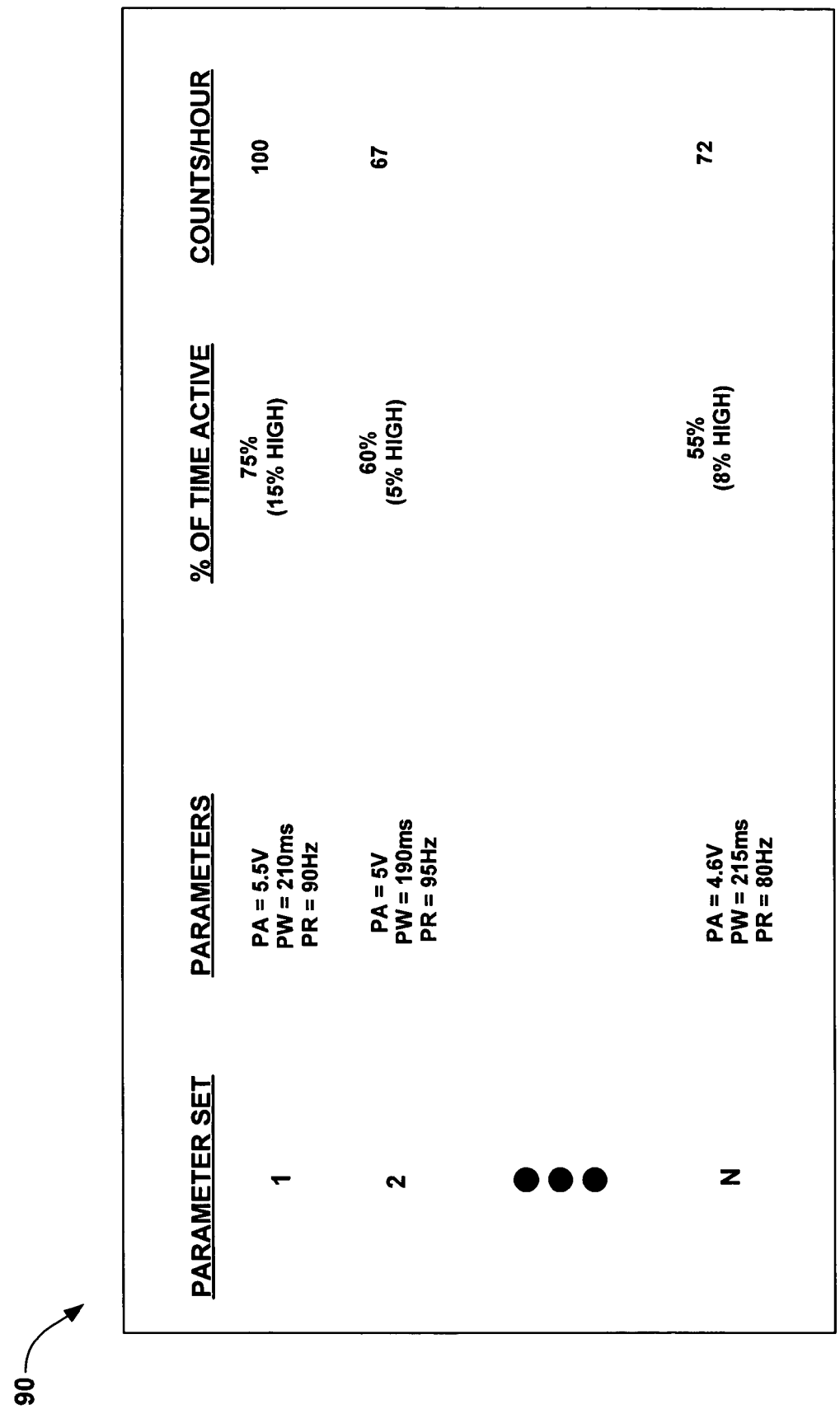
FIG. 6 illustrates an example list of therapy parameter sets and associated activity metric values that may be presented by a clinician programmer.

FIG. 6 illustrates an example list 90 of therapy parameter sets and associated activity metric values 66 that may be presented by clinician programmer 20. Each row of example list 90 includes an identification of one of therapy parameter sets 60, the parameters of the therapy parameter set, and values 66 associated with the therapy parameter set for each of two illustrated activity metrics. Programmer 20 may order list 90 according to a user-selected one of the activity metrics.

The activity metrics illustrated in FIG. 6 are a percentage of time active, and an average number of activity counts per hour. IMD 14 or programmer 20 may determine the average number of activity counts per hour for one of the illustrated therapy parameter sets by identifying the total number of activity counts associated with the parameter set and the total amount of time that IMD 14 was using the parameter set. IMD 14 or programmer 20 may determine the percentage of time active for one of parameter sets 60 by comparing each activity level 62 associated with the parameter set to an "active" threshold, and determining the percentage of activity levels 62 above the threshold. As illustrated in FIG. 9, IMD 14 or programmer 20 may also compare each activity level for the therapy parameter set to an additional, "high activity" threshold, and determine a percentage of activity levels 62 above that threshold.

Figure 7:
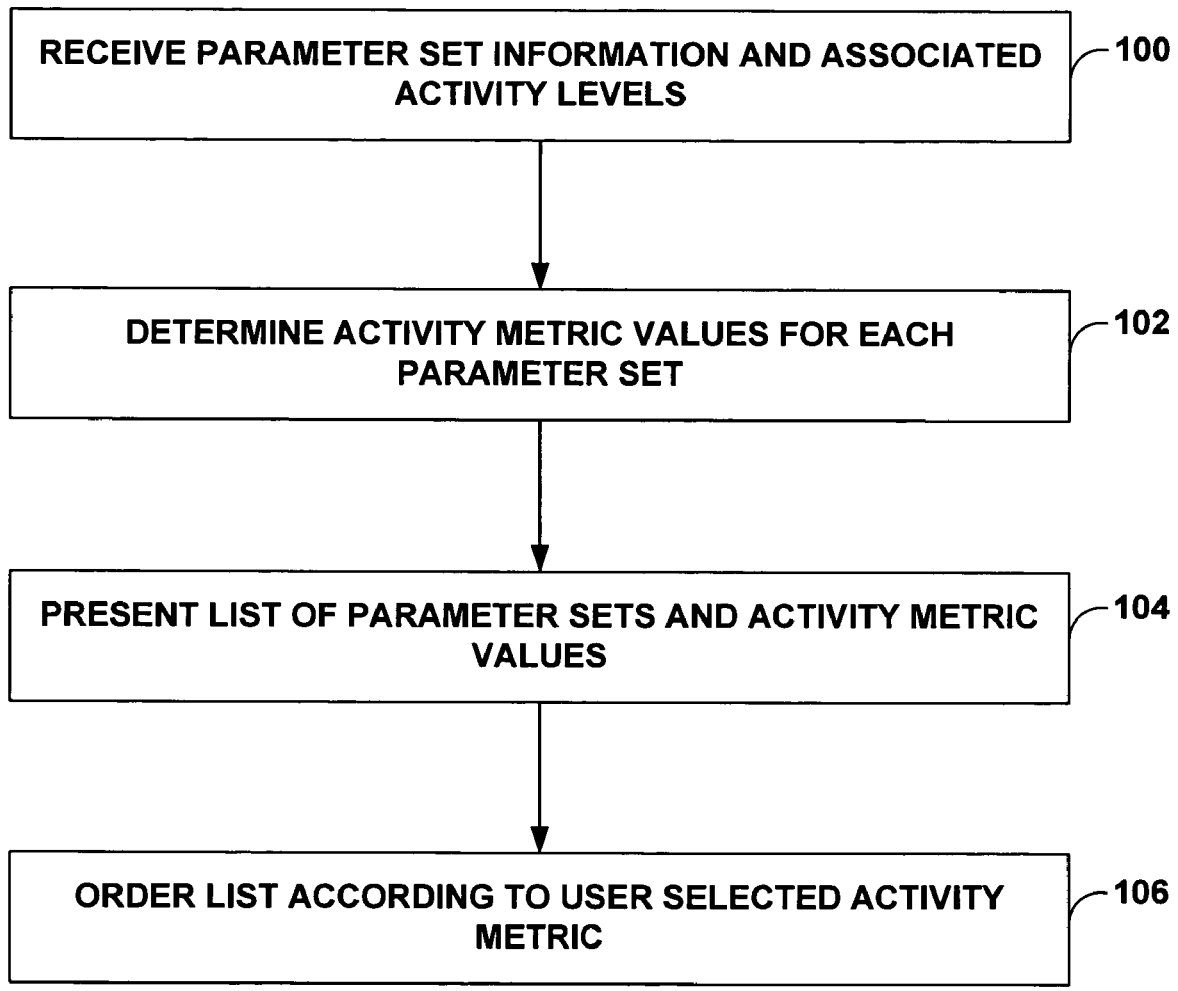
FIG. 7 is a flow diagram illustrating an example method for displaying a list of therapy parameter sets and associated activity metric values that may be employed by a clinician programmer.

FIG. 7 is a flow diagram illustrating an example method for displaying a list of therapy parameter sets 60 and associated activity metric values 66 that may be employed by a clinician programmer 20. Programmer 20 receives information identifying therapy parameter sets 60 and associated activity levels 62 from IMD 14 (100). Programmer 20 then determines one or more activity metric values 66 for each of the therapy parameter sets based on the activity levels 62 associated with the therapy parameter sets (102). In other embodiments, IMD 14 determines the activity metric values 66, and provides them to programmer 20, or provides samples of activity signals associated with therapy parameter sets to programmer 20 for determination of activity metric values, as described above. After receiving or determining activity metric values 66, programmer 20 presents a list 90 of therapy parameter sets 60 and associated activity metric values 66 to the clinician, e.g., via display 22 (104). Programmer 20 may order list 90 of therapy parameter sets 60 according to the associated activity metric values 66, and the clinician may select which of a plurality of activity metrics list 90 is ordered according to via a user interface 82 (106).

Various embodiments of the invention have been described. However, one skilled in the art will recognize that various modifications may be made to the described embodiments without departing from the scope of the invention. For example, although described herein primarily in the context of treatment of pain with an implantable neurostimulator, the invention is not so limited. The invention may be embodied in any implantable medical device that delivers a therapy, such as a cardiac pacemaker or an implantable pump. Further, the invention may be implemented via an external, e.g., non-implantable, medical device. In such embodiments, the external medical device itself may include a user interface and display to present activity information to a user, such as a clinician or patient, for evaluation of therapy parameter sets.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Activity metric values collected by the trial neurostimulator or pump may be used by a clinician to evaluate the prospective therapy parameter sets, and select parameter sets for use by the later implanted non-trial neurostimulator or pump. In particular, a trial neurostimulator or pump may determine values of one or more activity metrics for each of a plurality of prospective therapy parameter sets, and a clinician programmer may present a list of prospective parameter sets and associated activity metric values to a clinician. The clinician may use the list to identify potentially efficacious parameter sets, and may program a permanent implantable neurostimulator or pump for the patient with the identified parameter sets.

Further, the invention may be embodied as a computer-readable medium that includes instructions to cause a processor to perform any of the methods described herein. These and other embodiments are within the scope of the following claims.

The invention claimed is:

1. A method comprising:
   monitoring a signal that varies as a function of patient activity;
   periodically determining an activity level of the patient based on the signal;
   associating each of the determined activity levels with a therapy parameter set used by a medical device to deliver a therapy to a patient when the activity level was determined;
   determining a value of at least one activity metric for each of a plurality of therapy parameter sets based on activity levels associated with the therapy parameter sets, wherein determining a value of at least one activity metric comprises:
      comparing each of the activity levels associated with the therapy parameter set to a threshold value; and
      determining an average length of time that consecutively determined activity levels associated with the therapy parameter set were above the threshold.

2. The method of claim 1, wherein the signal comprises a signal generated by an accelerometer, the method further comprising filtering the signal to pass a band from approximately 0.1 Hz to approximately 10 Hz.

3. The method of claim 1, wherein periodically determining an activity level comprises:
   determining when the patient is awake; and
   periodically determining an activity level while the patient is determined to be awake.

4. The method of claim 1, wherein determining a value of at least one activity metric comprises determining at least one of a mean or a median of activity levels associated with the therapy parameter set.

5. The method of claim 4, wherein determining a value of at least one activity metric comprises:
   comparing the at least one of the mean or the median activity level to at least one threshold; and
   selecting the activity metric value from a plurality of predetermined possible activity metric values based on the comparison.

6. The method of claim 1, wherein determining a value of at least one activity metric for a therapy parameter set comprises:
   comparing each of the activity levels associated with the therapy parameter set to a threshold value; and
   determining at least one of a percentage of time above the threshold or a percentage of time below the threshold.

7. The method of claim 1, wherein periodically determining an activity level comprises periodically determining a number of activity counts.

8. The method of claim 7, wherein determining at least one activity metric value for each of a plurality of therapy parameter sets comprises determining an average number of activity counts per a unit of time for each of the plurality of therapy parameter sets based on the numbers of activity counts associated with the therapy parameter sets.

9. The method of claim 8, wherein determining an average number of activity counts per a unit of time comprises determining an average number of activity counts over a period of time substantially within a range from 10 to 60 minutes.

10. The method of claim 1, wherein periodically determining an activity level comprises periodically determining a value of at least one physiological parameter of the patient.

11. The method of claim 10, wherein periodically determining a value of a physiological parameter comprises periodically determining at least one of a heart rate, a respiration rate, respiratory volume, a core temperature, or a muscular activity level.

12. The method of claim 1, further comprising presenting a list of the plurality of therapy parameter sets and activity metric values associated with the therapy parameter sets.

13. The method of claim 12, further comprising ordering the list of therapy parameter sets according to the associated activity metric values.

14. The method of claim 13, wherein determining a value of at least one activity metric comprises determining a value of each of a plurality of activity metrics for each of a plurality of therapy parameter sets based on activity levels associated with the therapy parameter sets, and ordering the list comprises ordering the list according to a user selected one of the activity metrics.

15. The method of claim 1, wherein determining a value of at least one activity metric further comprises:
   determining a value of each of a plurality of activity metrics for each of the plurality of therapy parameter sets; and
   determining a value of an overall activity metric far each of the plurality of therapy parameter sets based on the plurality of activity metric values.

16. The method of claim 1, further comprising presenting a graphical representation of the determined activity levels.

17. The method of claim 16, wherein presenting a graphical representation comprises presenting at least one of a trend diagram, a histogram, or a pie chart based on the determined activity levels.

18. The method of claim 1, wherein the medical device comprises an implantable medical device.

19. The method of claim 18, wherein the implantable medical device comprises at least one of an implantable neurostimulator, or an implantable drug pump.

20. The method of claim 1, wherein the medical device comprises a trial neuro stimulator.

21. A medical system comprising:
a medical device that delivers a therapy to a patient; and
a processor that monitors a signal that varies as a function of patient activity, periodically determines an activity level of the patient based on the signal, associates each of the determined activity levels with a therapy parameter set used by the medical device to deliver the therapy to the patient when the activity level was determined, and determines a value of at least one activity metric for each of a plurality of therapy parameter sets based on activity levels associated with the therapy parameter sets,
wherein for each of the plurality of therapy parameter sets, the processor compares each of the activity levels associated with the therapy parameter set to a threshold value, and determines as an activity metric value for the parameter set an average length of time that consecutively determined activity levels were above the threshold.

22. The medical system of claim 21, wherein the medical device includes the processor.

23. The medical system of claim 21, further comprising a programming device that includes the processor.

24. The medical system of claim 21, wherein the signal comprises a signal generated by an accelerometer, and the medical device filters the signal to pass a band from approximately 0.1 Hz to approximately 10 Hz.

25. The medical system of claim 21, wherein the processor determines when the patient is awake, and periodically determines an activity level of the patient while the patient is determined to be awake.

26. The medical system of claim 21, wherein, for each of the therapy parameter sets, the processor determines at least one of a mean or a median of activity levels associated with the therapy parameter set.

27. The medical system of claim 26, wherein, for each of the therapy parameter sets, the processor compares the at least one of the mean or the median activity level to at least one threshold, and selects another activity metric value from a plurality of predetermined possible activity metric values based on the comparison.

28. The medical system of claim 21, wherein, for each of the therapy parameter sets, the processor compares each of the activity levels associated with the therapy parameter set to a threshold value, and determines as another activity metric value for the therapy parameter set at least one of a percentage of time above the threshold and a percentage of time below the threshold.

29. The medical system of claim 21, wherein an activity level comprises a number of activity counts.

30. The medical system of claim 29, wherein another activity metric value for each of the therapy parameter sets comprises an average number of activity counts per a unit of time.

31. The medical system of claim 30, wherein the unit of time is substantially within a range from 10 to 60 minutes.

32. The medical system of claim 21, wherein the processor periodically determines an activity level by periodically determining a value of at least one physiological parameter of the patient.

33. The medical system of claim 32, wherein the processor periodically determines at least one of a heart rate, a respiration rate, a respiratory volume, a core temperature, or a muscular activity level.

34. The medical system of claim 21, further comprising a display to present a list of the plurality of therapy parameter sets and activity metric values associated with the therapy parameter sets.

35. The medical system of claim 34, further comprising a programming device that includes the display.

36. The medical system of claim 35, wherein the programming device orders the list of therapy parameter sets according to the associated activity metric values.

37. The medical system of claim 36, wherein the processor determines a value of each of a plurality of activity metrics for each of the plurality of therapy parameter sets based on activity levels associated with the therapy parameter sets, and the programming device orders the list according to a user selected one of the activity metrics.

38. The medical system of claim 34, wherein the medical device includes the display, and the processor generates the list and presents the list via the display.

39. The medical system of claim 21, wherein the processor determines a value of each of a plurality of activity metrics, and determines a value of an overall activity metric based on the plurality of activity metric values.

40. The medical system of claim 21, further comprising a programming device that includes a display, wherein the programming device presents a graphical representation of the activity levels determined by the medical device via the display.

41. The medical system of claim 40, wherein the programming device presents at least one of a trend diagram, a histogram, or a pie chart via the display based on the activity levels determined by the medical device.

42. The medical system of claim 21, wherein the medical device comprises an implantable medical device.

43. The medical system of claim 42, wherein the implantable medical device comprises at least one of an implantable neurostimulator or an implantable drug pump.

44. The medical system of claim 21, wherein the medical device comprises a trial neurostimulator.

45. A medical system comprising:
means for monitoring a signal that varies as a function of patient activity via a medical device that delivers a therapy to a patient;
means for periodically determining an activity level of the patient based on the signal;
means for associating each of the determined activity levels with a therapy parameter set that was used by a medical device to deliver a therapy to a patient when the activity level was determined;
means for determining a value of an activity metric for each of a plurality of therapy parameter sets based on activity levels associated with the therapy parameter sets; and
means for presenting a list of the plurality of therapy parameter sets and activity metric values associated with the therapy parameter sets.

46. The medical system of claim 45, further comprising means for ordering the list according to the activity metric values.

47. The medical system of claim 46, further comprising means for determining a value of each of a plurality of activity metrics for each of a plurality of therapy parameter sets based on activity levels associated with the therapy parameter sets, wherein the means for ordering the list comprises means for ordering the list according to a user selected one of the activity metrics.

48. A computer-readable medium comprising instructions that cause a programmable processor to:
receive information identifying a plurality of therapy parameter sets and associated activity levels from an implantable medical device;
determine a value of an activity metric for each of a plurality of therapy parameter sets based on activity levels associated with the therapy parameter sets; and
present a list of the plurality of therapy parameter sets and activity metric values associated with the therapy parameter sets.

49. The medium of claim 48, wherein the instructions that cause the processor to determine a value of an activity metric comprise instructions that cause the processor to, for each of the therapy parameter sets, determine at least one of a mean and a median of activity levels associated wit the therapy parameter set.

50. The medium of claim 49, wherein the instructions that cause the processor to determine a value of an activity metric comprise instructions that cause the processor to, for each of the therapy parameter sets:
compare the at least one of the mean and the median activity level to at least one threshold; and
select an activity metric value from a plurality of predetermined possible activity metric values based on the comparison.

51. The medium of claim 48, wherein the instructions that cause the processor to determine a value of an activity metric comprise instructions that cause the processor to, for each of the therapy parameter sets:
compare each of the activity levels associated with the therapy parameter set to a threshold value; and
determine as the activity metric value for the therapy parameter set at least one of a percentage of time above the threshold and a percentage of time below the threshold.

52. The medium of claim 48, wherein the instructions that cause the processor to determine a value of an activity metric comprise instructions that cause the processor to, for each of the plurality of parameter sets:
compare each of the activity levels associated with the therapy parameter set to a threshold value; and
determine as the activity metric value for the parameter set an average length of time that consecutively determined activity levels were above the threshold.

53. The medium of claim 48, wherein an activity level comprises a number of activity counts, the instructions that cause the processor to determine a value of an activity metric comprise instructions that cause the processor determine an average number of activity counts per a unit of time.

54. The medium of claim 48, further comprising instructions that cause the processor to order the list of therapy parameter sets according to the associated activity metric values.

55. The medium device of claim 54,
wherein the instructions that cause the processor to determine a value of an activity metric comprise instructions that cause the processor to determine a value of each of a plurality of activity metrics for each of the plurality of therapy parameter sets based on activity levels associated with the therapy parameter sets,
the medium further comprising instructions that cause the processor to:
receive a selection of one of the activity metrics from a user; and order the list according to the user selected one of the activity metrics.

56. A method comprising:
monitoring a signal that varies as a function of patient activity;
periodically determining an activity level of the patient based on the signal;
associating each of the determined activity levels with a therapy parameter set used by a medical device to deliver a therapy to a patient when the activity level was determined;
for each of the therapy parameter sets, determining at least one of a mean or a median of activity levels associated with the therapy parameter set;
comparing the at least one of the mean or the median activity level for each of the therapy parameter sets to at least one threshold; and
selecting an activity metric value for each of the therapy parameter sets from a plurality of predetermined possible activity metric values based on the comparison.

57. A medical system comprising:
a medical device that delivers a therapy to a patient; and
a processor that monitors a signal that varies as a function of patient activity, periodically determines an activity level of the patient based on the signal, associates each of the determined activity levels with a therapy parameter set used by the medical device to deliver the therapy to the patient when the activity level was determined, for each of the parameter sets, determines at least one of a mean or a median of activity levels associated with the therapy parameter set, compares the at least one of the mean or the median activity level for each of the therapy parameter sets to at least one threshold, and selects an activity metric value for each of the therapy parameter sets from a plurality of predetermined possible activity metric values based on the comparison.

58. A method comprising:
monitoring a signal that varies as a function of patient activity;
periodically determining an activity level of the patient based on the signal;
associating each of die determined activity levels with a therapy parameter set used by a medical device to deliver a therapy to a patient when the activity level was determined;
determining a value of at least one activity metric for each of a plurality of therapy parameter sets based on activity levels associated with the therapy parameter sets; and
presenting a list of the plurality of therapy parameter sets and activity metric values associated with the therapy parameter sets.

59. The method of claim 58, further comprising ordering the list of therapy parameter sets according to the associated activity metric values.

60. The method of claim 59, wherein determining a value of at least one activity metric comprises determining a value of each of a plurality of activity metrics for each of a plurality of therapy parameter sets based on activity levels associated with the therapy parameter sets, and ordering the list comprises ordering the list according to a user selected one of the activity metrics.

61. The method of claim 58, wherein periodically determining an activity level comprises:
determining when the patient is awake; and
periodically determining an activity level while the patient is determined to be awake.

* * * * *

UNITED STATES PATENT AND TRADEMARK OFFICE
CERTIFICATE OF CORRECTION

| | | |
|---|---|---|
| PATENT NO. | : 7,395,113 B2 | Page 1 of 1 |
| APPLICATION NO. | : 10/825965 | |
| DATED | : July 1, 2008 | |
| INVENTOR(S) | : Kenneth T. Heruth | |

It is certified that error appears in the above-identified patent and that said Letters Patent is hereby corrected as shown below:

<u>Column 20</u>

Line 40, "each of die" should read -- each of the --.

Line 46, "parameter sets;" should read -- parameters sets; --.

Signed and Sealed this

Twentieth Day of January, 2009

JON W. DUDAS
*Director of the United States Patent and Trademark Office*